United States Patent
Goruganthu (10) Patent No.: US 9,304,308 B2
(45) Date of Patent: Apr. 5, 2016

(54) LASER SCANNING MODULE INCLUDING AN OPTICAL ISOLATOR

(75) Inventor: Rama R. Goruganthu, Austin, TX (US)

(73) Assignee: ADVANCED MICRO DEVICES, INC., Sunnyvale, CA (US)

( * ) Notice: Subject to any disclaimer, the term of this patent is extended or adjusted under 35 U.S.C. 154(b) by 754 days.

(21) Appl. No.: 13/593,970

(22) Filed: Aug. 24, 2012

(65) Prior Publication Data

US 2012/0320455 A1 Dec. 20, 2012

Related U.S. Application Data

(63) Continuation-in-part of application No. 12/653,235, filed on Dec. 9, 2009, now Pat. No. 8,537,464.

(51) Int. Cl.
| | |
|---|---|
| G02B 21/00 | (2006.01) |
| G02B 21/10 | (2006.01) |
| G02B 27/28 | (2006.01) |
| G01N 21/47 | (2006.01) |
| G01N 21/956 | (2006.01) |

(52) U.S. Cl.
CPC ............ G02B 21/0052 (2013.01); G01N 21/47 (2013.01); G02B 21/0032 (2013.01); G02B 21/10 (2013.01); G02B 27/286 (2013.01); G01N 21/956 (2013.01); G01N 2021/4709 (2013.01); G01N 2021/4733 (2013.01); G01N 2021/4735 (2013.01)

(58) Field of Classification Search
None
See application file for complete search history.

(56) References Cited

U.S. PATENT DOCUMENTS

| | | | |
|---|---|---|---|
| 5,291,012 A | | 3/1994 | Shimizu |
| 5,768,015 A | * | 6/1998 | Pattie ....................... 359/484.03 |
| 5,912,766 A | * | 6/1999 | Pattie ....................... 359/484.03 |
| 6,088,491 A | * | 7/2000 | Sorin et al. ..................... 385/11 |
| 6,249,619 B1 | * | 6/2001 | Bergmann et al. .............. 385/11 |
| 6,445,453 B1 | | 9/2002 | Hill |
| 6,449,091 B1 | * | 9/2002 | Cheng et al. ............. 359/484.04 |
| 6,492,638 B2 | * | 12/2002 | Hoffmann ..................... 250/234 |
| 6,642,517 B1 | | 11/2003 | Ghislain |
| 6,760,158 B1 | * | 7/2004 | Cao ........................... 359/484.04 |
| 6,816,300 B2 | * | 11/2004 | Shirai et al. ................... 359/280 |
| 6,919,989 B1 | | 7/2005 | Deng |
| 6,947,619 B2 | * | 9/2005 | Fujita et al. ..................... 385/11 |
| 2001/0009541 A1 | | 7/2001 | Ueyanagi |
| 2007/0290145 A1 | * | 12/2007 | Viellerobe et al. .......... 250/459.1 |
| 2008/0308730 A1 | * | 12/2008 | Vizi et al. ....................... 250/309 |
| 2009/0231692 A1 | | 9/2009 | Yoshida |
| 2011/0134520 A1 | | 6/2011 | Goruganthu |

* cited by examiner

*Primary Examiner* — Derek S Chapel
(74) *Attorney, Agent, or Firm* — Park, Vaughan, Fleming & Dowler LLP (57) ABSTRACT

The present application discloses various implementations of a laser scanning module. In one implementation, such a laser scanning module comprising an optical isolator including first and second linear polarizers, a collimating optics configured to receive light produced by a laser light source and to pass a substantially collimated light beam to the first linear polarizer, and a scanning unit situated to receive light passed by the second linear polarizer. The first linear polarizer is separated from the collimating optics by a first distance less than a second distance separating the second linear polarizer from the scanning unit.

11 Claims, 7 Drawing Sheets

LASER SCANNING MODULE INCLUDING AN OPTICAL ISOLATOR

This application is a continuation-in-part of, and claims benefit of the filing date of, and hereby incorporates fully by reference, the pending parent application entitled "Optical Isolation Module and Method for Utilizing the Same," Ser. No. 12/653,235, filed on Dec. 9, 2009 now U.S. Pat. No. 8,537,464.

BACKGROUND

Laser scanning microscopy is widely used in semiconductor fabrication. For example laser scanning microscopy may be used to perform soft defect localization, in which soft defects, such as timing marginalities, are detected in fabricated semiconductor devices. Soft defect localization typically utilizes a laser to scan regions of a semiconductor device under test. As the dimensions of modern semiconductor devices become ever smaller, the resolution required to isolate individual device features for soft defect analysis grows correspondingly higher.

High resolution imaging of semiconductor devices can be achieved through use of a dark field microscopy approach employing a solid immersion lens (SIL). In order for such an approach to achieve the imaging resolution required by the smallest device dimensions, the imaging light incident on the target should be supercritical light, capable of producing evanescent fields within the semiconductor material housing the target. In addition, it may be necessary to collect the light scattered from the target along or near the central axis of the SIL. Consequently, a laser scanning module capable of creating supercritical light using an optical isolator to scan a target while concurrently enabling collection of light scattered by such a target is a desirable feature for use in laser scanning microscopy.

SUMMARY

The present disclosure is directed to a laser scanning module including an optical isolator, as shown in and/or described in connection with at least one of the figures, and as set forth more completely in the claims.

DETAILED DESCRIPTION

The following description contains specific information pertaining to implementations in the present disclosure. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

Figure 1:
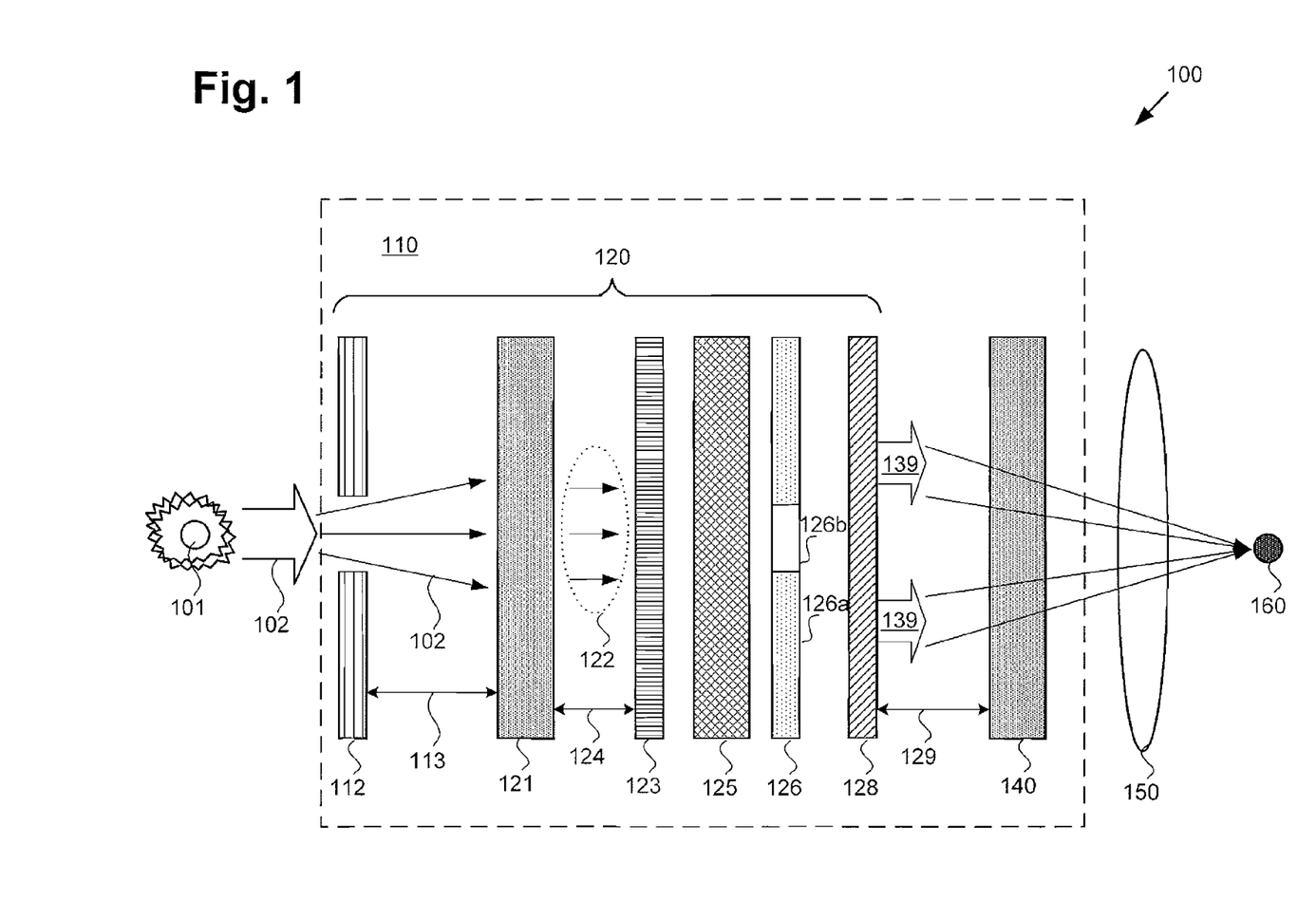
FIG. 1 shows a diagram of a laser scanning microscopy system including an exemplary implementation of a laser scanning module including an optical isolator.

FIG. 1 is a diagram of a laser scanning microscopy system including an exemplary implementation of a laser scanning module including an optical isolator. Laser scanning microscopy system 100 includes laser light source 101 producing light 102 for use in imaging target 160, objective lens 150, and laser scanning module 110 situated between laser light source 101 and objective lens 150. Laser scanning module 110 is shown to include optical isolator 120 and scanning unit 140. It is noted that although scanning unit 140 is depicted as an integrated block component, or unit, in the interests of conceptual clarity, scanning unit 140 may include multiple internal features, such as a galvanometer scanner including scanning mirrors, and one or more scanning lenses, for example (mirrors and lenses not shown as such in FIG. 1). Laser scanning microscopy system 100 may be implemented to perform soft defect analysis of target 160, which may take the form of an integrated circuit (IC) fabricated on a semiconductor wafer or die.

Optical isolator 120 includes at least first linear polarizer 123, Faraday rotator 125, transmissive element 126 including half-wave plate 126a and aperture 126b, and second linear polarizer 128. As shown in FIG. 1, Faraday rotator 125 and transmissive element 126 including half-wave plate 126a and aperture 126b are situated between first linear polarizer 123 and second linear polarizer 128. Optionally, and as further shown by FIG. 1, in some implementations, optical isolator 120 may include one or both of inlet aperture 112, which may be a confocal inlet aperture, and collimating optics 121. That is to say, in some implementations, inlet aperture 112 and/or collimating optics 121, may not be included in optical isolator 120, but rather constitute separate components of laser scanning module 110. It is noted that in implementations in which optical isolator 120 omits collimating optics 121, optical isolator 120 is situated within laser scanning module 110 between collimating optics 121 and scanning unit 140.

First linear polarizer 123 is separated from collimating optics 121 by first distance 124, while second linear polarizer 128 is separated from scanning unit 140 by second distance 129. It is noted that in at least one implementation, first distance 124 separating first linear polarizer 123 from collimating optics 121 is less than, and may be substantially less than, second distance 129 separating second linear polarizer 128 from scanning unit 140. For example, in one implementation, first distance 124 may be approximately one millimeter (1 mm) and second distance 129 may be approximately 2 mm. Also shown in FIG. 1 are spacing 113, substantially collimated light beam 122, and annulus of light 139 produced by optical isolator 120 from substantially collimated light beam 122.

As will be explained below in greater detail, laser scanning module 110 including optical isolator 120 is configured to receive light 102, to produce annulus of light 139, and to utilize scanning unit 140 to scan target 160 using annulus of light 139. In addition, and as will also be described in detail below, optical isolator 120 of laser scanning module 110 is configured to enable collection of light scattered by target 160.

Figure 2:
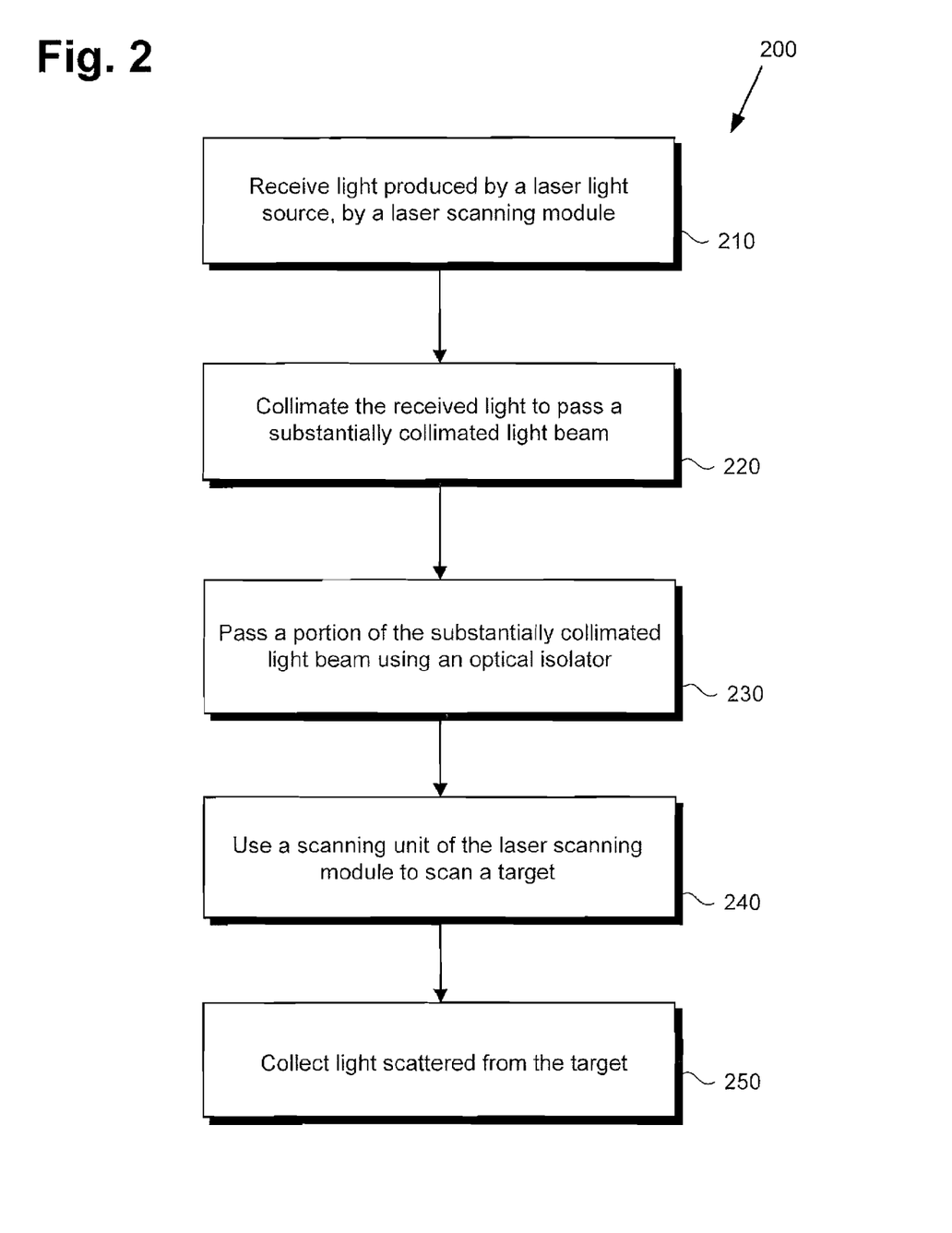
FIG. 2 shows a flowchart presenting one exemplary implementation of a method for performing laser scanning microscopy.

The functionality of laser scanning module 110 will be further described by reference to FIG. 2, which shows a flowchart presenting one exemplary implementation of a method for performing laser scanning microscopy. With respect to the method outlined in FIG. 2, it is noted that certain details and features have been left out of flowchart 200 in order not to obscure the discussion of the inventive features in the present application.

Referring to flowchart 200 with additional reference to laser scanning microscopy system 100, FIG. 1, flowchart 200 begins with laser scanning module 110 receiving light 102 produced by laser light source 101 (210). Light 102 produced by laser light source 101 may be received by laser scanning module 110 and admitted into optical isolator 120 through inlet aperture 112. It is reiterated that inlet aperture 112 for admitting light 102 may be included as part of optical isolator 120, or may be present as a separate component of laser scanning module 110, as explained above.

Flowchart 200 continues when collimating optics 121 collimates light 102 received through inlet aperture 112 so as to pass substantially collimated light beam 122 (220). As shown in FIG. 1, collimating optics 121 is configured to receive light 102 produced by laser light source 101, and to pass substantially collimated light beam 122 to first linear polarizer 123.

According to one implementation, collimating optics 121 may include an achromatic doublet lens having a focal length corresponding to spacing 113. In implementations in which inlet aperture is a confocal inlet aperture, for example, spacing 113 may be substantially equal to a focal length of collimating optics 121. As a specific example, in one implementation, collimating optics 121 may have a focal length of approximately 50 mm, and inlet aperture 112 may be a confocal inlet aperture spaced apart from collimating optics 121 by spacing 113 also substantially equal to 50 mm.

Flowchart 200 continues with use of optical isolator 120 to pass a portion of substantially collimated light beam 122 (230). As shown in FIG. 1, according to one implementation, optical isolator 120 is configured to receive substantially collimated light beam 122 at first linear polarizer 123, and to pass annulus of light 139 from second linear polarizer 128. An exemplary process by which optical isolator 120 produces annulus of light 139 from substantially collimated light beam 122 will be further described by reference to FIGS. 3, 4, 5A, 5B, and 5C below.

Flowchart 200 continues with use of scanning unit 140 to scan target 160 (240). Scanning unit 140 is situated to receive light passed by second polarizer 128, e.g., annulus of light 139, and is configured to use that light to scan target 160. Scanning unit 140 may include a galvanometer scanner and a scanning lens or lenses, as explained above. Scanning of target 160 by scanning unit 140 may proceed using any suitable techniques. One such technique using a solid immersion lens (SIL) to perform dark field microscopy will be described by reference to FIGS. 3, 4, 5A, 5B, and 5C below.

Flowchart 200 concludes with collection of light scattered from target 160 (250). An exemplary implementation using optical isolator 120 of laser scanning module 110 to enable collection of light scattered by target 160 will also be described below by reference to FIGS. 3, 4, 5A, 5B.

Figure 3:
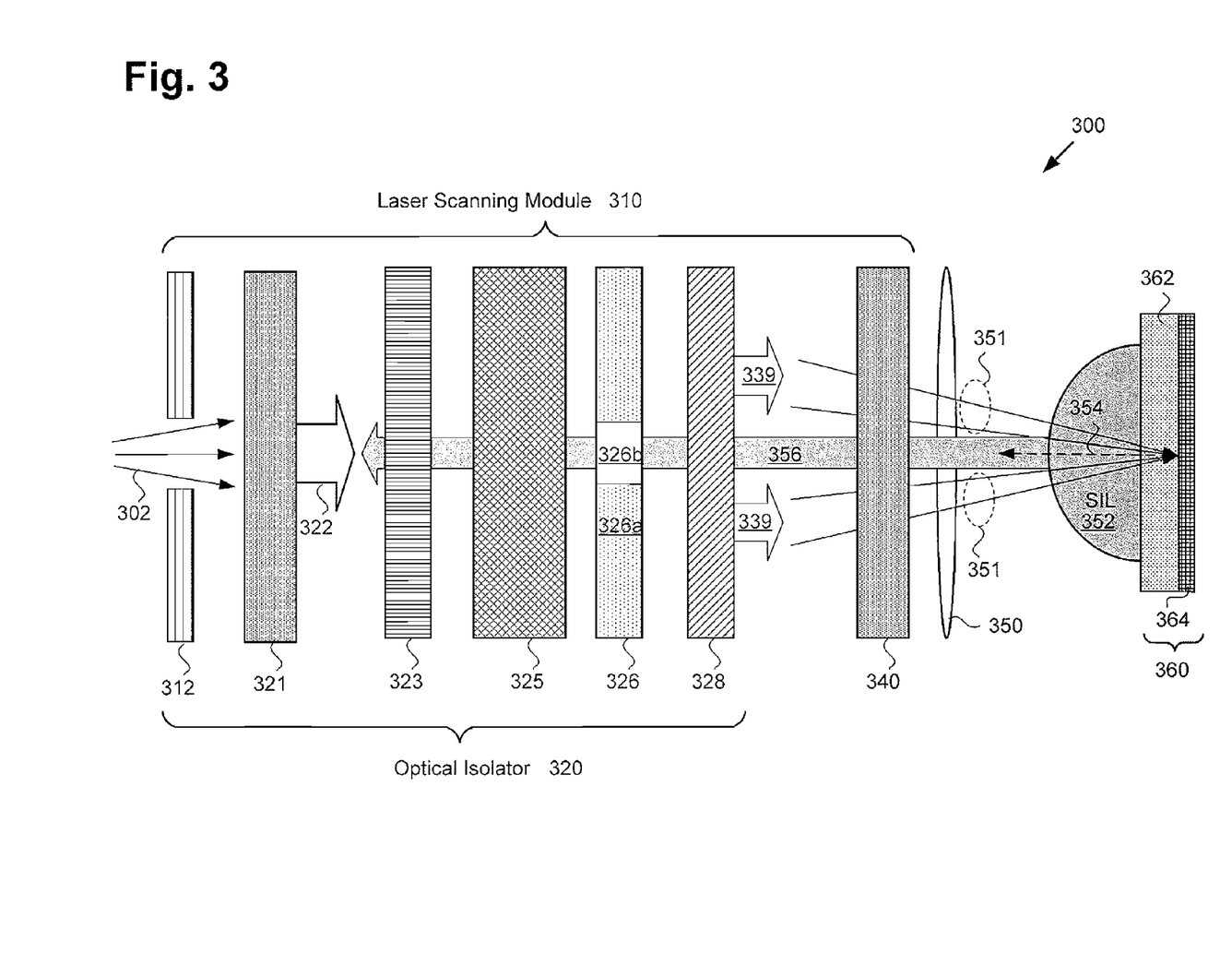
FIG. 3 shows a diagram of a portion of an exemplary laser scanning microscopy system implemented to perform dark field microscopy, which includes the exemplary laser scanning module of FIG. 1.

Referring now to FIG. 3, FIG. 3 shows a diagram of a portion of an exemplary laser scanning microscopy system implemented to perform dark field microscopy, which includes the exemplary laser scanning module of FIG. 1. Laser scanning microscopy system 300 includes laser scanning module 310 including optical isolator 320 and scanning unit 340, objective lens 350, SIL 352, and target 360, such as the backside of semiconductor wafer or die 362, for example, on which circuit 364 is fabricated. Also shown in FIG. 3 are light 302, substantially collimated light beam 322, substantially supercritical incident light rays 351, and scattered light 356 collected from target 360.

Optical isolator 320 includes first linear polarizer 323, Faraday rotator 325, transmissive element 326 including half-wave plate 326a and aperture 326h, and second linear polarizer 328. In addition, in some implementations, as depicted in FIG. 3, optical isolator 320 may include inlet aperture 312 and/or collimating optics 321. Laser scanning module 310 including optical isolator 320 and scanning unit 340 corresponds to laser scanning module 110 including optical isolator 120 and scanning unit 140, in FIG. 1. Moreover, inlet aperture 312, collimating optics 321, first linear polarizer 323, Faraday rotator 325, transmissive element 326, and second linear polarizer 328, in FIG. 3, correspond respectively to inlet aperture 112, collimating optics 121, first linear polarizer 123, Faraday rotator 125, transmissive element 126, and second linear polarizer 128, in FIG. 1. Laser scanning microscopy system 300 may be implemented to perform soft defect analysis of semiconductor devices fabricated as part of circuit 364 on semiconductor wafer or die 362.

According to the implementation of FIG. 3, light 302 is admitted through inlet aperture 312 from a light source of laser scanning microscopy system 300 (light source not shown in FIG. 3), such as a laser light source corresponding to laser light source 101, in FIG. 1. Light 302 is received by collimating optics 321, which passes substantially collimated light beam 322 to first linear polarizer 323. Substantially collimated light beam 322 is then filtered and manipulated by optical isolator 320 to produce annulus of light 339 passed by second linear polarizer 328.

Annulus of light 339 is received by scanning unit 340, which is configured to scan target 360 through objective lens 350 and SIL 352, using substantially supercritical incident light rays 351. Thus, light enters laser scanning module 310 as light 302 and exits laser scanning module as substantially supercritical incident rays 351. In addition, scattered light 356 from target 360, traveling along or near central optical axis 354 of SIL 352 can then be collected through optical isolator 320 for use in imaging semiconductor devices of circuit 364.

As will be explained below in greater detail, depending on the particular configuration of optical isolator 320, optical isolator 320 may be configured to receive either light 302 or substantially collimated light beam 322, and to produce annulus of light 339 shaped so as to provide substantially supercritical incident rays 351, as well as to enable collection of scattered light 356 along central optical axis 354 of SIL 352.

It is noted that although FIG. 3 shows optical isolator 320 as comprising particular elements in a particular order, in other implementations, optical isolator 320 may have an arrangement other than that shown in FIG. 3. Thus, although the implementation of FIG. 3 represents Faraday rotator 325 as being situated between first linear polarizer 323 and transmissive element 326, in other implementations, transmissive element 326 may be interposed between first linear polarizer 323 and Faraday rotator 325.

It is further noted that the specific implementational environment represented in FIGS. 3, 4, 5A, 5B, and 5C is shown for conceptual clarity, and is not to be interpreted as a limitation. As shown and discussed in the present application, the present inventive concepts have applicability to high resolution imaging of semiconductor devices. More generally, however, the present concepts may be utilized to enable laser scanning microscopy on nano-materials and biological samples, as well as semiconductor dies, either packaged or on wafer.

Use of laser scanning module 310 including optical isolator 320 to perform optical isolation as part of a laser scanning microscopy process will now be further described in conjunction with FIGS. 4, 5A, 5B, and 5C. With respect to the method outlined in FIG. 4, it is noted that certain details and features have been left out of flowchart 400 in order not to obscure the discussion of the inventive features in the present application.

Figure 4:
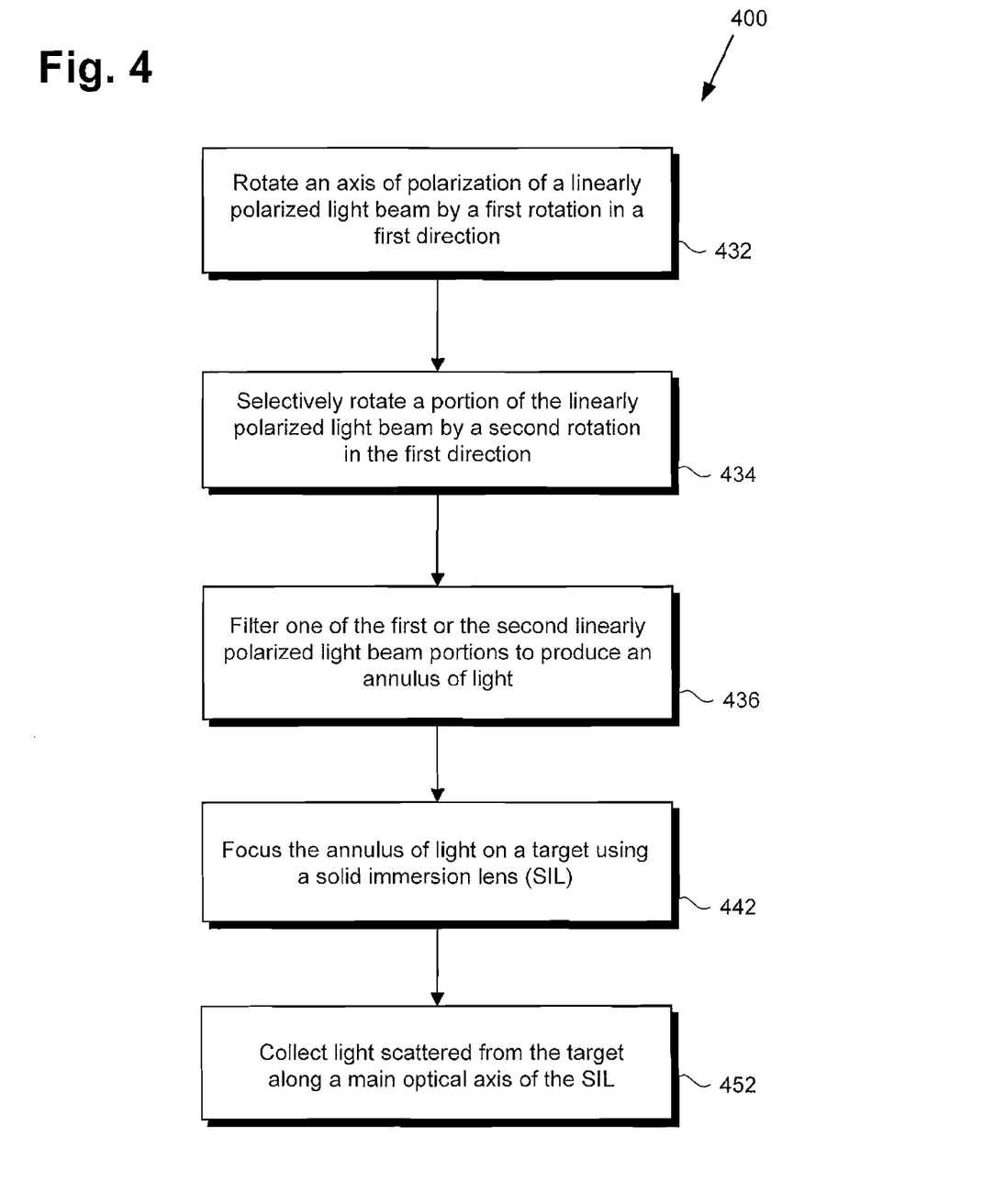
FIG. 4 shows a flowchart presenting one exemplary implementation of a method for performing optical isolation as part of a laser scanning microscopy process.
Figure 5A:
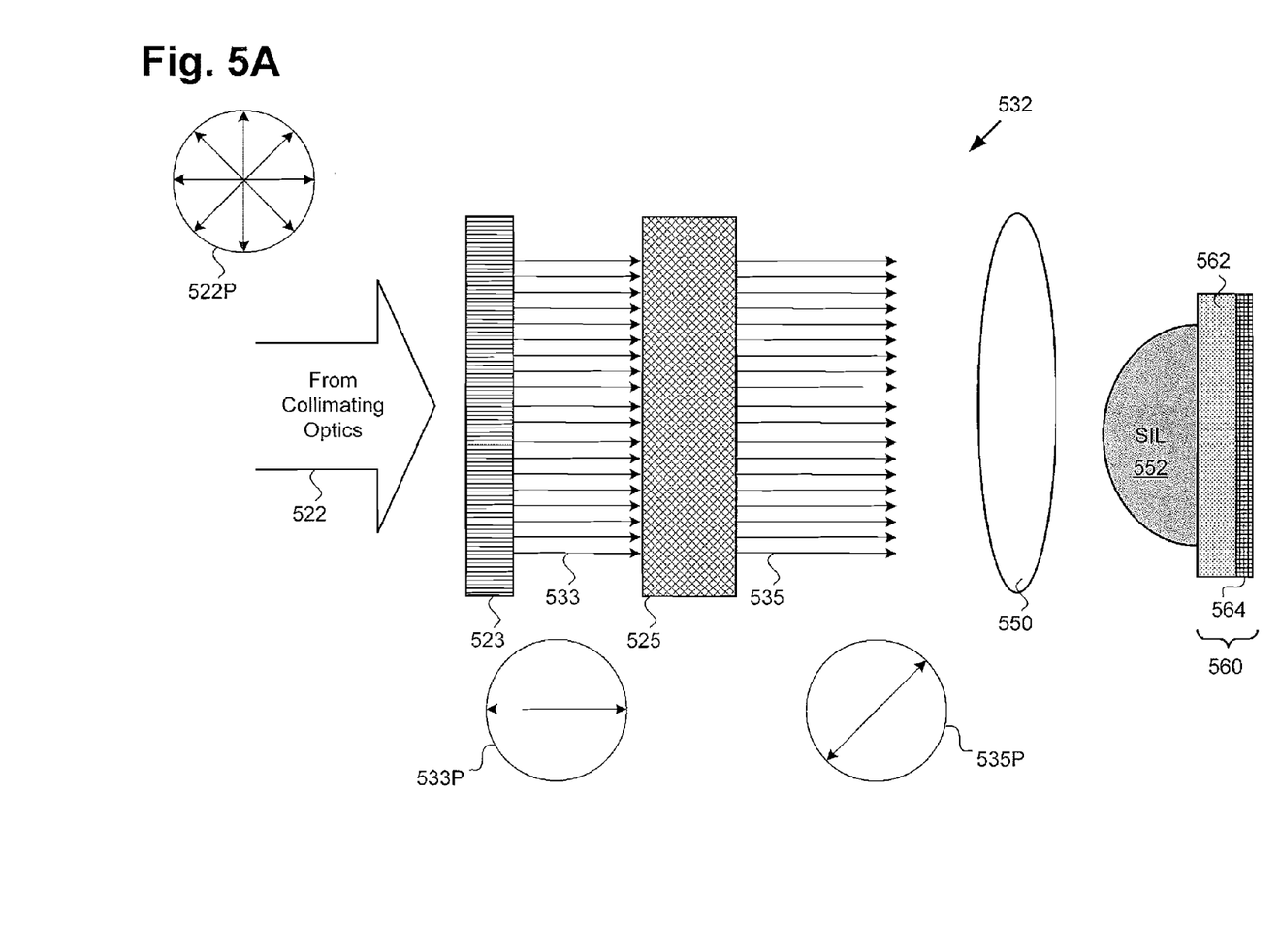
FIG. 5A is a diagram showing a portion of the laser scanning module of FIG. 3 at an early stage of the example method shown in FIG. 4, according to one exemplary implementation.

Referring to FIG. 5A, FIG. 5A shows laser scanning environment 532 including a portion of laser scanning module 310, of FIG. 3, at an early stage of the example method shown by flowchart 400, in FIG. 4. Laser scanning environment 532 includes substantially collimated light beam 522, first linear polarizer 523, Faraday rotator 525, objective lens 550, SIL 552, and target 560 including semiconductor wafer or die 562 and circuit 564.

Substantially collimated light beam 522, first linear polarizer 523, Faraday rotator 525, objective lens 550, SIL 552, and target 560 correspond respectively to substantially collimated light beam 122/322, first linear polarizer 123/323, Faraday rotator 125/325, objective lens 150/350, SIL 352, and target 160/360, in FIG. 1/3. In addition, transmissive element 526 including half-wave plate 526a and aperture 526b introduced in FIG. 5B corresponds to transmissive element 126/326 including half-wave plate 126a/326a and aperture 126b/326b, in FIG. 1/3. Moreover, optical isolator 520 including first linear polarizer 523, Faraday rotator 525, transmissive element 526, and second linear polarizer 528, in FIG. 5C, corresponds to optical isolator 120/320 of laser scanning module 110/310, in FIG. 1/3. Also shown in FIG. 5A is polarization diagram 522P of substantially collimated light beam 522, as well as linearly polarized light 533, first rotated imaging light 535, and their respective polarization diagrams 533P and 535P.

Laser scanning environment 532 shows the optical isolation process performed by laser scanning module 110/310 including optical isolator 120/320, according to one exemplary implementation, at an early stage of such a process. Moreover, referring to FIGS. 5B and 5C, respective laser scanning environments 534 and 536 show the results of the optical isolation process performed by laser scanning module 110/310 including optical isolator 120/320 at intermediate stages of the exemplary method of flowchart 400.

Referring to flowchart 400 with additional reference to laser scanning environment 532, in FIG. 5A, flowchart 400 begins with rotating an axis of polarization of substantially linearly polarized light beam 522 by a first rotation in a first direction (432). As shown by polarization diagram 522P, it is contemplated that substantially collimated light beam 522 may arrive at first linear polarizer 523 in an unpolarized state. First linear polarizer 523, which is represented as a horizontal polarizer, passes linearly polarized light 533 having a horizontal axis of polarization, as shown by polarization diagram 533P. As further shown by polarization diagram 535P, the first rotation in the first direction is performed by Faraday rotator 525 and imposes a 45° anti-clockwise rotation on linearly polarized light 533 passed by first linear polarizer 523.

It is noted that although the implementation of FIG. 5A represents first linear polarizer 523 as a horizontal polarizer, that characterization is merely exemplary. In other implementations, first linear polarizer 523 may impose an axis of polarization having any angular deflection on substantially collimated light beam 522. Moreover, because linearly polarized light 533 may have an angle of polarization other than zero degrees) (0°), i.e., polarized light 533 may not be horizontally polarized, the 45° anti-clockwise rotation imposed on linearly polarized light 533 by Faraday rotator 525 may result in first rotated imaging light 535 having a polarization other than that shown by polarization diagram 535P.

Figure 5B:
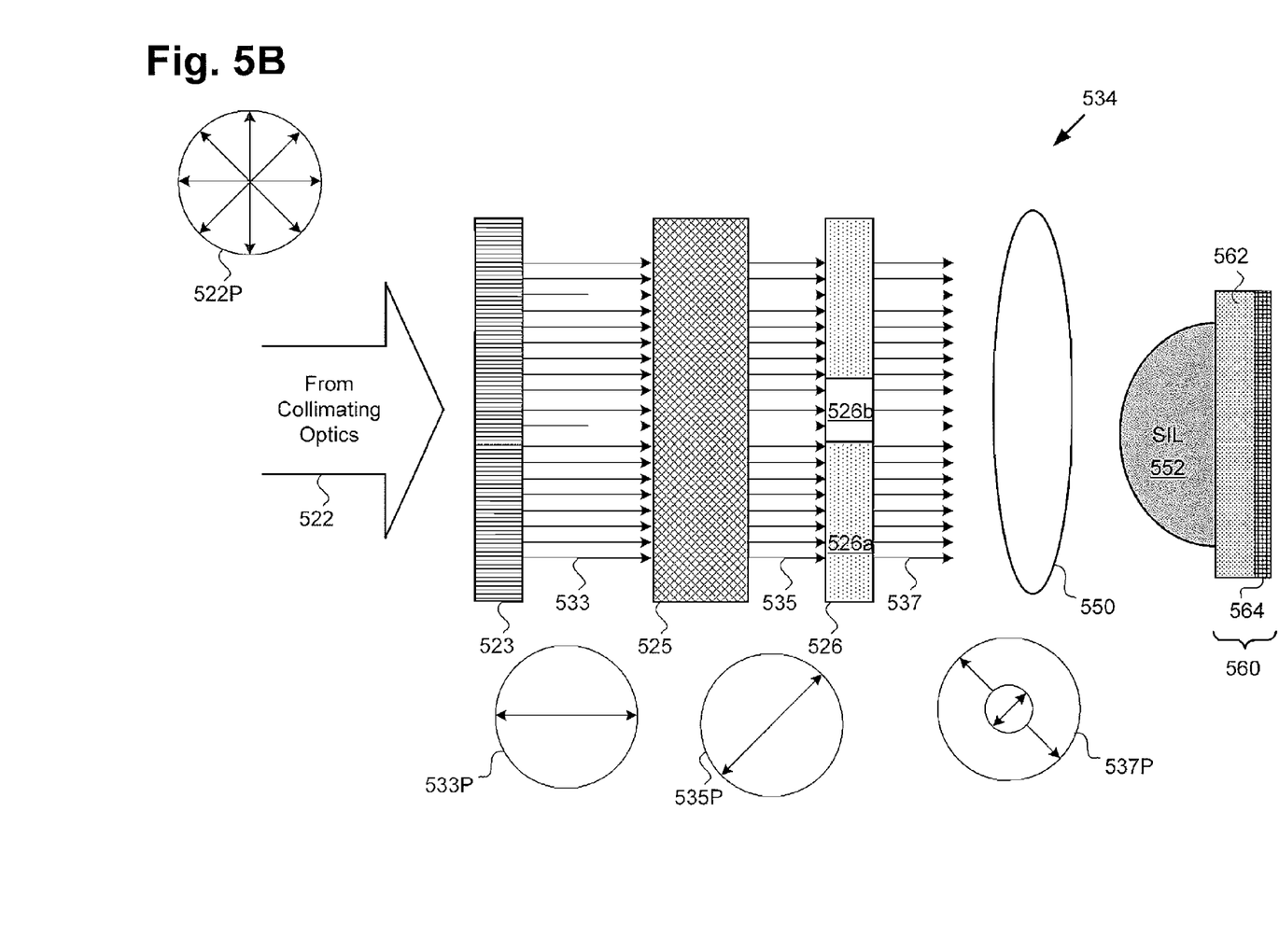
FIG. 5B is a diagram showing a portion of the laser scanning module of FIG. 3 at an intermediate stage of the example method shown in FIG. 4, according to one exemplary implementation.

Referring now to laser scanning environment 534, in FIG. 5B, in conjunction with FIG. 4, flowchart 400 continues with selective rotation of a portion of first rotated imaging light 535 by a second rotation in the first direction (434). Such a selective rotation may be performed by transmissive element 526. As noted, transmissive element 526 includes half-wave plate 526a. In the present implementation, that arrangement is represented by annular half-wave plate 526a (shown in cross-section in FIG. 5B) surrounding central aperture 526b of transmissive element 526, which may include a circular aperture having a diameter of approximately 2.3 mm, for example. As a result, the portion of first rotated imaging light 535 passing through half-wave plate 526a is rotated an additional ninety degrees (90°) in the anti-clockwise direction, while the portion passing through aperture 526b is not further rotated. Thus, the selective rotation produces optically isolated imaging light 537 comprising a first linearly polarized light beam portion, e.g., the portion passing through aperture 526b of transmissive element 526 and having undergone only the first rotation imposed by Faraday rotator 525, and a second linearly polarized light beam portion, e.g., the portion passing through half-wave plate 526a of transmissive element 526 and having undergone a second 90° rotation in the same direction as the 45° first rotation imposed by Faraday rotator 525.

Consequently, as shown by polarization diagram 537P, optically isolated imaging light 537 passing from transmissive element 526 is characterized by an annular portion having an axis of polarization perpendicular to the axis of polarization of its central portion. As further shown by polarization diagram 537P, the present exemplary method results in an annular light beam portion having passed through half-wave plate 526a and having an axis of polarization rotated by one hundred thirty-five degrees (135°) anti-clockwise, and a central light beam portion having passed through aperture 526b and having an axis of polarization rotated by 45° anti-clockwise.

Figure 5C:
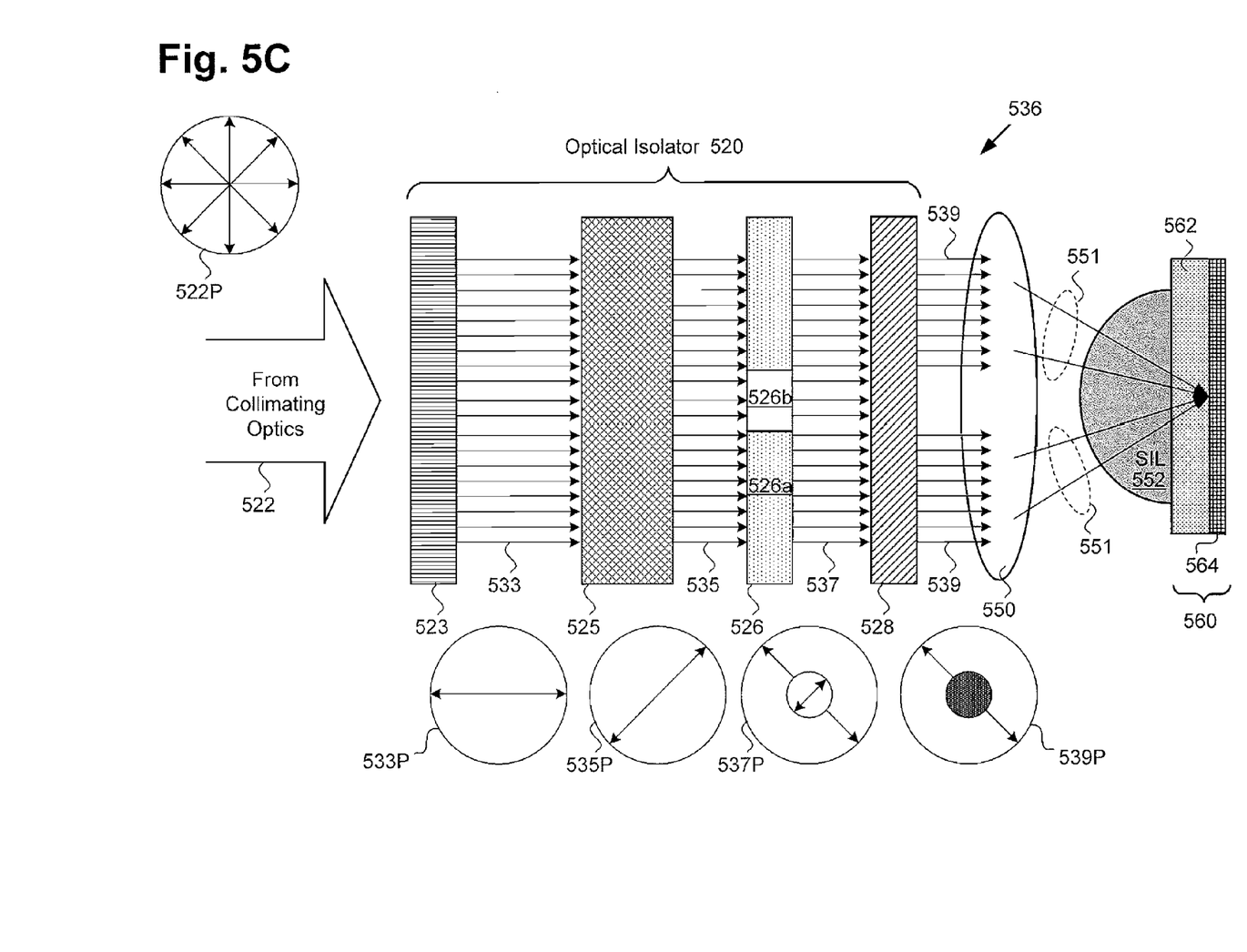
FIG. 5C is a diagram showing a portion of the laser scanning module of FIG. 3 at another intermediate stage of the example method shown in FIG. 4, according to one exemplary implementation.

Moving now to laser scanning environment 536, in FIG. 5C with continued reference to FIG. 4, flowchart 400 continues with filtering one of the two linearly polarized light beams produced thus far to produce annulus of light 539 (436). According to the implementation of FIG. 5C, the described filtering corresponds to filtering optically isolated imaging light 537, having two linearly polarized portions with their respective axes of polarization perpendicular to one another, using second linear polarizer 528 having its axis of polarization selected to transmit the annular light beam portion. Because the axis of polarization of the central light beam portion is perpendicular to that of the annular portion, it is also substantially perpendicular to the polarization axis of second linear polarizer 528, causing the central portion of the polarized light beam to be blocked.

Thus, according to the present implementation, second linear polarizer 528 has its axis of polarization set at 135°, thereby substantially passing annulus of light 539, as shown by polarization diagram 539P, in which the central section is represented as dark to indicate blockage of the central portion of optically isolated imaging light 537 by second linear polarizer 528. Although the foregoing discussion of various components of optical isolator 520 describes one possible implementational model, there are numerous variations. For example, exchanging the locations of Faraday rotator 525 and transmissive element 526 would produce substantially the same cumulative rotation of the respective first and second portions of optically isolated imaging light 537, as is achieved by the implementation of FIG. 5C.

Moreover, in another implementation, transmissive element 526 may have its central section occupied by a half-wave plate, rather than aperture 526b, the outer annular region being configured so as to impose substantially no rotation on the transmitted light. In that implementation, annular portion of optically isolated imaging light 537 would undergo a single rotation of 45°, due to passage through Faraday rotator 525, while the central portion of optically isolated imaging light 537 would be rotated twice, producing a cumulative rotation of 135° for that central portion. Simple substitution of second linear polarizer 528 with a linear polarizer having its polarization axis set to 45°, rather than 135°, would once again substantially transmit annulus of light 539 while substantially blocking the central portion of optically isolated imaging light 537.

Flowchart 400 continues with focusing annulus of light 539 on target 560, such as circuit 564 fabricated on semiconductor wafer or die 562, using SIL 552 (442). Focusing of annulus of light 539 on target 560 may correspond to SIL 552 receiving substantially supercritical incident rays 551 from the laser scanning module including optical isolator 520 and a scanning unit, through objective lens 550 (scanning unit omitted from FIG. 5C due to the emphasis on optical isolation in that figure). As a result, SIL 552 may be utilized to image individual devices in circuit 564 using the supercritical imaging light provided by the laser scanning module including optical isolator 520.

Referring back to FIG. 3, flowchart 400 concludes with collecting light scattered from target 360 along central optical axis 354 of SIL 352 (452). By way of example, we invoke the sample implementational details ascribed to the implementation shown by FIGS. 5A through 5C. That is to say, let us assume that first linear polarizer 323 is a horizontal polarizer, transmissive element 326 includes annular half-wave plate 326a and aperture 326b, and that the polarization axis of second linear polarizer 328 is selected so as to pass annulus of light 339 to SIL 352.

In that implementational setting, scattered light 356 directed along central optical axis 354 of SIL 352 (hereinafter "near-axis scattered light 356") is unaffected by scanning unit 340, is polarized by second linear polarizer 328, passes substantially unaltered through aperture 326b of transmissive element 326, and is rotated by 45° in a clockwise direction by Faraday rotator 325. As a result, near-axis scattered light 356 encounters first linear polarizer 323 as horizontally polarized light and is substantially passed to a detector of laser scanning microscopy system 300 as a result (detector not shown in FIG. 3). It is noted that the described clockwise rotation of near-axis scattered light 356 is the result of the unique properties of a Faraday rotator, in which the direction of rotation produced by the Faraday rotator changes according to the direction of light propagation through the Faraday rotator, as is known in the art. Thus, having Faraday rotator 325 as a component of optical isolator 320 included in laser scanning module 310 results in anti-clockwise rotation of linearly polarized light traveling towards SIL 352, but clockwise rotation of light traveling away from SIL 352, thereby enabling collection of near-axis scattered light 356.

More generally, collection of near-axis scattered light 356 from target 360 includes linearly polarizing near-axis scattered light 356, e.g., by second linear polarizer 328, and selectively rotating a portion of the linearly polarized scattered light by a third rotation in the first direction to produce first and second linearly polarized scattered light portions. In other words, the off-axis portions of the scattered light (off-axis scattered light not shown in FIG. 3) passing through half-wave plate 326a are rotated 90° anti-clockwise, while near-axis scattered light 356 is not rotated during passage through aperture 326b. The collection of near-axis scattered light 356 further includes rotating the first and second linearly polarized scattered light portions in a second direction opposite the first direction by a fourth rotation, e.g., 45° clockwise rotation of both the off-axis scattered light and near-axis scattered light 356. As a result, near-axis scattered light 356 undergoes only the fourth rotation, while the off-axis scattered light portion undergoes both the third and fourth rotations. Subsequent filtering by first linear polarizer 323 results in blockage of the off-axis scattered light and allows passage and collection of near-axis scattered light 356 traveling along central optical axis 354.

More generally still, although the present exemplary collection of light scattered by target 360 has been described in terms of specific design parameters, consideration of the implementational variations discussed above reveals that the all of the various implementations of laser scanning module 310 including optical isolator 320 described in the present application can be configured to (1) deliver annulus of light 339 comprising substantially supercritical incident rays 351 while concurrently substantially blocking subcritical imaging light components, and (2) collect near-axis scattered light 356 traveling along central optical axis 354 of SIL 352.

The present inventor has realized that a substantial portion of the light scattered from a target semiconductor device as a result of the evanescent fields produced in a wafer or die by laser scanning microscopy system 300 is directed along central optical axis 354. As a result, significant advantages accrue from providing a solution capable of blocking a subcritical central portion of an imaging light beam along a central optical axis in order to deliver substantially supercritical imaging light to the target device, and of collecting near-axis scattered light 356 to enhance image brightness and contrast.

As discussed above, the present application discloses a laser scanning module and system that desirably enables the delivery of substantially supercritical imaging light components, the blocking of substantially subcritical imaging light components, and the highly advantageous selective collection of light scattered from a target. As a result, implementations of the present inventive concepts can provide lateral resolution on the order of fifty nanometers (50 nm). In addition, the laser scanning module disclosed by the present application lends itself to implementation in a laser scanning microscopy system capable of rapidly and efficiently imaging devices fabricated on a semiconductor wafer or die. Furthermore, because implementations of the present laser scanning module can be implemented in combination with a SIL, the disclosed solution represents a robust approach to IC and device imaging, and for circuit analysis applications such as soft defect localization.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described above, but many rearrangements, modifications, and substitutions are possible without departing from the scope of the present disclosure.

The invention claimed is:

1. A laser scanning module comprising:
an optical isolator including first and second linear polarizers;
a collimating optics configured to receive light produced by a laser light source and to pass a substantially collimated light beam to said first linear polarizer;
a scanning unit situated to receive light passed by said second linear polarizer; and
a transmissive element including a half-wave plate, said transmissive element situated between said first and second linear polarizers, said half-wave plate comprising an aperture located therein;
wherein a first portion of light passing through said transmissive element passes through said half-wave plate, causing, by said half-wave plate, a rotation of a corresponding angle in an axis of polarization of said first portion and wherein a second portion of light passing through said transmissive element passes through said aperture without changing an axis of polarization of said second portion.

2. The laser scanning module of claim 1, wherein said optical isolator includes said collimating optics.

3. The laser scanning module of claim 1, wherein said optical isolator further comprises a Faraday rotator, said Faraday rotator situated between said first and second linear polarizers.

4. The laser scanning module of claim 1,
wherein light passed by said transmissive element passes to said second linear polarizer; and
wherein said second linear polarizer passes said first portion and blocks said second portion.

5. A laser scanning microscopy system comprising:
a laser light source and an objective lens;
a laser scanning module situated between said laser light source and said objective lens, said laser scanning module including:
an optical isolator including first and second linear polarizers;
a collimating optics configured to receive light produced by said laser light source and to pass a substantially collimated light beam to said first linear polarizer;
a scanning unit situated to receive light passed by said second linear polarizer; and
a transmissive element including a half-wave plate, said transmissive element situated between said first and second linear polarizers, said half-wave plate comprising an aperture located therein;
wherein a first portion of light passing through said transmissive element passes through said half-wave plate, causing, by said half-wave plate, a rotation of a corresponding angle in an axis of polarization of said first portion and wherein a second portion of light passing through said transmissive element passes through said aperture without changing an axis of polarization of said second portion.

6. The laser scanning microscopy system of claim 5, wherein said optical isolator includes said collimating optics.

7. The laser scanning microscopy system of claim 5, wherein said optical isolator further comprises a Faraday rotator, said Faraday rotator situated between said first and second linear polarizers.

8. The laser scanning microscopy system of claim 5,
wherein light passed by said transmissive element passes to said second linear polarizer; and
wherein said second linear polarizer passes said first portion and blocks said second portion.

9. A method for performing laser scanning, said method comprising:
receiving, by a laser scanning module, light produced by a laser light source;
collimating said light to pass a substantially collimated light beam;
passing a portion of said substantially collimated light beam by an optical isolator of said laser scanning module, said passing of said portion of said substantially collimated light beam by said optical isolator comprising:
passing said substantially collimated light beam through a transmissive element in said optical isolator, said transmissive element comprising a half-wave plate having an aperture located therein, and wherein passing said substantially collimated light beam through said transmissive element comprises:
causing, by said half-wave plate, a rotation of a corresponding angle in an axis of polarization of a first portion of said substantially collimated light beam that passes through said half-wave plate; and
passing a second portion of said substantially collimated light beam through said aperture without changing an axis of polarization of said second portion; and
performing said laser scanning by a scanning unit of said laser scanning module.

10. The method of claim 9, further comprising focusing a portion of said substantially collimated light beam passed by said optical isolator on a target.

11. The method of claim 9, wherein passing said portion of said substantially collimated light beam by said optical isolator comprises:
passing said first portion and said second portion from said transmissive element to a second linear polarizer in said optical isolator, wherein said second linear polarizer passes said first portion and blocks said second portion.

* * * * *